United States Patent [19]

Kussick

[11] Patent Number: 4,997,182
[45] Date of Patent: Mar. 5, 1991

[54] TONGUE THRUST CORRECTIVE DEVICE

[76] Inventor: Leon Kussick, 1 Surrey La., Livingston, N.J. 07039

[21] Appl. No.: 420,175

[22] Filed: Oct. 12, 1989

[51] Int. Cl.$^5$ .......................... A63B 23/00; A61F 5/56
[52] U.S. Cl. ........................................ 272/95; 128/861
[58] Field of Search ................. 272/95; 128/860, 861, 128/15

[56] References Cited

U.S. PATENT DOCUMENTS

| | | | |
|---|---|---|---|
| 3,871,370 | 3/1975 | McDonald | 128/860 |
| 4,185,817 | 1/1980 | Peterson | 128/861 |
| 4,718,662 | 1/1988 | North | 272/95 |

*Primary Examiner*—Stephen R. Crow

[57] ABSTRACT

An oral appliance adapted to redirect improper positioning of the tongue and lips at the start of a swallow comprises a molded body of acrylic or similar material having an arcuate marginal segment curved to contact the occlusal surfaces of teeth of the upper dental arch, an upper tongue positioning segment and a lower tongue positioning segment. The marginal segment has thin, substantially flat and relatively wide upper side surfaces that are separated to span a prescribed range of dental arches. The upper side surfaces are tightly engaged to the side teeth by a shaped layer of light activated resin for retention while the wearer is active or at rest. The lower tongue positioning segment forms an inclined channel below the marginal segment with a posteriorly facing entrance for receiving the inferior surface of the anterior portion of the tongue and the upper tongue positioning segment forms a channel above the marginal segment with a posteriorly facing entrance for receiving the superior surface of the anterior portion of the tongue. An aperture formed in the upper tongue positioning segment directs the apex of the tongue into contact with the curved aspect of the anterior palate and soft tissue.

19 Claims, 3 Drawing Sheets

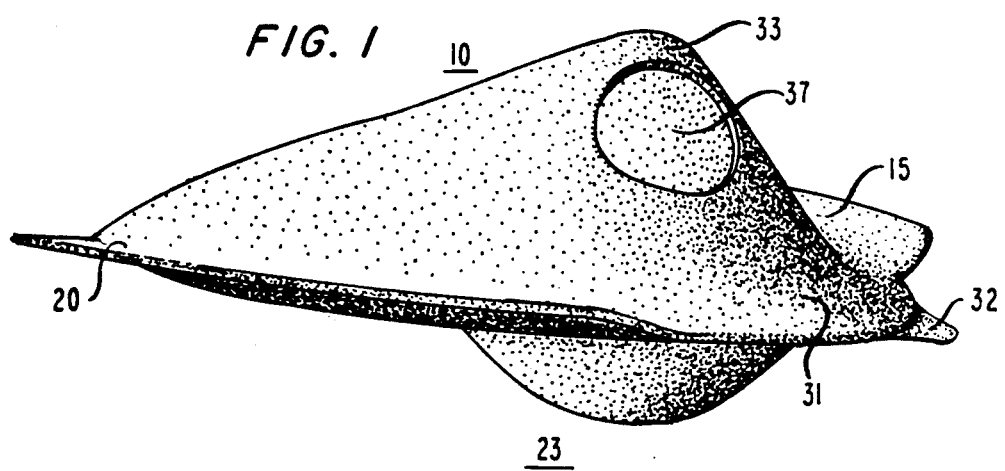
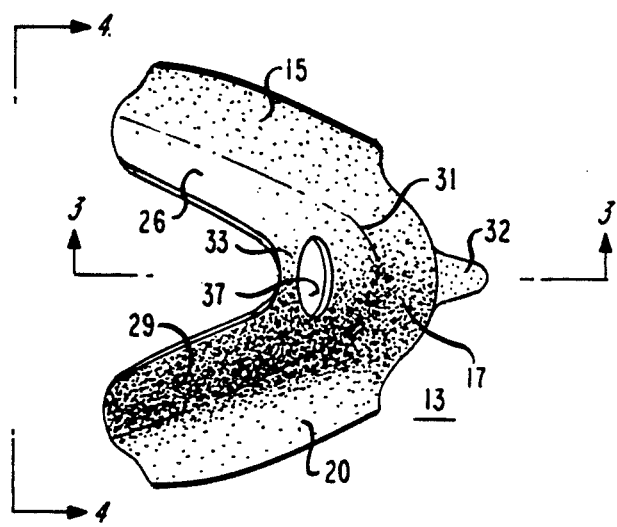
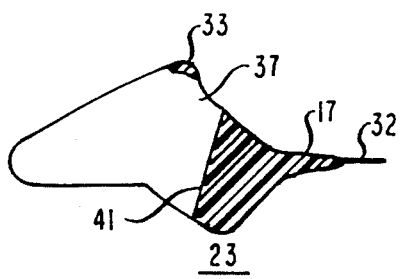

4,997,182

TONGUE THRUST CORRECTIVE DEVICE

FIELD OF THE INVENTION

The invention relates to oral corrective appliances and more particularly to devices adapted to correct tongue thrust problems.

BACKGROUND OF THE INVENTION

In normal swallowing as described in the article "Radiographic Study of Movements of the Tongue in Swallowing" by G.M. Adrian et al. appearing in The Dental Practitioner, Vol. V No. 8, April, 1955 at pages 252–261, the tip of the tongue is positioned against the anterior curved surface of the palate just behind the upper anterior dentition. The superior surface of the tongue is then elevated upwards and backwards against the hard palate. When the front of the tongue is raised at the start of the swallow the arched dorsal surface is lowered and the forepart of the soft palate is depressed and bowed forward into the mouth cavity. A seal is thereby maintained between the tongue and palate. If the tongue tip is held too far forward and too low in the mouth as swallowing begins, it is thrust forward against or between the backs of the front teeth. The substantial force exerted on the teeth during poor swallowing often causes an abnormal repositioning of the front teeth and surrounding bone. An habitual incorrect placement of the tongue when swallowing, i.e., tongue thrust, may cause a serious problem such as anterior open bite.

U.S. Pat. No. 3,478,742 issued to E. H. Bohlmann Nov. 18, 1969 discloses an orthodontic multipurpose repositioner and oral habit conditioner comprising a molded plastic support, guard and barrier device fitted between the teeth of a patient for tooth, lip and tongue positioning. The device has sockets to receive the upper and lower teeth, extension parts for lip positioning and a barrier to prevent insertion of a thumb into the mouth and/or protrusion of the tongue between the teeth. A tongue guide extending upwardly along the roof of the mouth carries electrodes to repel the tongue downward by galvanic action which stimulates reflex tongue movement. The tongue tip, however, is deflected downward. But as stated in the aforementioned article, the ideal position is against the anterior bend of the hard palate behind the front teeth.

U.S. Pat. No. 3,871,370 issued to L. E. McDonald Mar. 18, 1975 discloses a tongue thrust correction appliance positionable in a patient's mouth. The appliance has an upper jaw engaging structure including two laterally spaced elements and a shelf-like plate. The plate is integrally molded with the laterally spaced elements for suspension across the interior of the mouth in spaced relationship to the roof of the mouth. Each of the laterally spaced elements is provided with surface conformations that enhance retentive engagement with the jaw. The lateral spaced elements maintain the plate in suspended relationship for support of the endmost portion of the tongue on the upper surface of the plate. Tongue movement is thereby and restricted to a predetermined position against the roof of the mouth during swallowing. The tongue tip, however, may fall below the shelf-like plate so that neither proper positioning nor proper physiologic posture is assured at the start of the swallow.

U.S. Pat. No. 4,718,662 issued to R. B. North Jan. 12, 1988 discloses a tongue positioning and exercising device having an outer marginal area for clenched retention between upper and lower teeth. Tongue supporting members extend inwardly and upwardly from the marginal area to position the tongue properly with the tongue tip in contact with the upper alveolar ridge of the gum. Openings permit passage of saliva through the device. Projections on a modified form of the device cause tongue discomfort if the tongue is improperly located below the device. The device, however, requires clenched retention so that normal mouth opening is not possible.

"Bone Remodeling Orthodontics by Jaw Repositioning and Alveolar Growth" by Leon Kussick Copyrighted 1987 by Quintessence Publishing Co. Inc., Chicago, Ill. discloses at page 244 an acrylic maxillary removable tongue thrust retraining appliance having an assembly of Adams clasps arranged for retention, a labial arch wire positioned to retract flared maxillary anteriors and a lingual strengthening wire adapted to the patient. The assembly is formed individually for each patient. Portions of the assembly that should not have acrylic are blocked out by an appropriate material. Acrylic is then poured to provide an anterior tongue channel so to direct the tongue to a hole cut in the anterior part of the palatal acrylic. In primary dentition, retention can be provided by occlusal acrylic extended around buccal teeth. Clasps as used in the aforementioned appliance are subject to deformation. In all cases, the devices are constructed from impressions made for individual patients.

In order to fabricate any of the foregoing tongue thrust retraining appliances for an individual patient, it is necessary to take impressions of and construct models of the individual patient's mouth. A mold for the appliance is then prepared from the models and the molded appliance is fitted to the mouth of the patient. The process is time consuming and requires expert care at each step. It is an object of the invention to provide an improved tongue thrust retraining device readily adapted to fit a wide range of patients without requiring impressions and models in its preparation. It is a further object of the invention to provide an improved tongue thrust retraining device which is adapted to simulate the physiological aspects of proper swallowing.

BRIEF SUMMARY OF THE INVENTION

The invention is directed to an appliance adapted to redirect improper positioning of the tongue and lips at the start of a swallow commonly known as tongue thrust habit. The appliance comprises a body of acrylic or similar material having an arcuate marginal segment curved to contact the occlusal surfaces of teeth of the upper dental arch. The marginal segment has a substantially flat and relatively wide upper surface that spans a prescribed range of dental arches. A tongue positioning segment includes a lower member that forms an inclined channel below the marginal segment with a posteriorly facing entrance for receiving the inferior surface of the anterior portion of the tongue and an upper member that forms a channel above the marginal segment with a posteriorly facing entrance for receiving the superior surface of the anterior portion of the tongue. An aperture formed in the upper member of the tongue positioning segment directs the tip of the tongue into contact with the anterior curved aspect of the palate and soft tissue.

According to one aspect of the invention, the device is prefabricated to fit a prescribed range of dental arches and the wide upper surface of the marginal segment is retained on the upper lateral or buccal dentition of a particular patient having a dental arch within the prescribed range.

According to another aspect of the invention, the front facing portion of the marginal segment is relieved and sloped forward and downward below incisal edges of the anterior teeth of the upper jaw and extends forward over the anterior dentition of the lower jaw to prevent the lower lip from engaging behind already flared upper front teeth. The upper anterior teeth are then free to drop downward and backward.

BRIEF DESCRIPTION OF THE DRAWINGS

FIG. 1 is a perspective view of a tongue thrust retraining device illustrative of the invention;

FIG. 2 is a top plan view of the device;

FIG. 3 is an elevational view of the device as seen along line 3—3 of FIG. 2;

DETAILED DESCRIPTION

Figure 4:
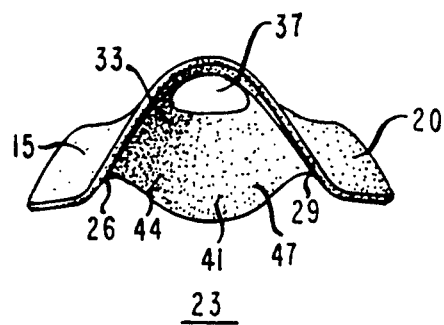
FIG. 4 is a rear elevational view of the device as seen along line 4—4 of FIG. 2.

A tongue thrust retraining device illustrating the invention is shown in perspective in FIG. 1. FIGS. 2 through 5 show various views of the device. Referring to these figures, the device comprises a body 10 constructed of acrylic or like plastic material. The body 10 has a generally planar marginal member 13 curved to conform to the line of the posterior dentition of the upper jaw. After adaptation to provide proper fit and retention in the mouth of a particular patient as shown in FIG. 5, marginal member 13 is removably retained by the posterior dentition e.g. 91, 92, 93 of the upper jaw. The patient may open and close his or her mouth in normal fashion while wearing the corrective device. Member 13 is relatively thin, e.g. 3 to 5 mm, so that the resting length of the lower jaw muscles is not exceeded. Marginal member 13 includes left side section 15, front section 17 and right side section 20. The side sections 15 and 20 are relatively wide as shown in the top plan view of FIG. 2 to meet the posterior biting surfaces of the upper dentition of a wide range of mouths. These side sections are also relatively flat so that the device may be fitted on and removably retained by the side teeth of the upper jaw of a wide range of patients as will be described. Front section 17 projects forward to the incisal edges of the upper front teeth 51 in FIG. 5 to prevent contact between the lingual aspect of the upper anterior teeth and the lower lip while swallowing or at rest. For patients with flared upper front teeth, front section 17 may be sloped to extend over the lower front dentition to the plane of the incisal edges of the flared teeth 51 as indicated in FIG. 5.

As shown in the sectional view of FIG. 3, The device has a tongue directing segment which comprises lower ramp member 23 below the marginal member 13 and upper ramp member 33 above marginal member 13. Ramp 23 is angled backward and downward from the bottom of front section 17 of marginal member 13 and the palatal bridge of ramp 33 is angled backward and upward from front section 17. Ramp member 23 may, for example, be 6 mm thick at its intersection with marginal member 13 and may taper down to a thickness of 2 mm. These ramp 23 and 33 channel the tongue tip to the proper position for initiating normal swallowing. Upper ramp 33 has an aperture 37 therein which is located adjacent to the curved aspect of the palate anterior bend of the palate when inserted in a patient's mouth. The shape of aperture 37 is such that it accommodates the apex of the tongue and may vary from that shown in the top plan view of FIG. 2. Aperture 37 is made large enough, e.g. 10 mm, so that the tip of the tongue engages the soft palatal tissue. Lower ramp 23 is adapted to guide the inferior and lateral surfaces of the anterior portion of the tongue upward during forward movement. Narrow upper ramp 33 constrains the superior anterior surface of the tongue so that the apex thereof is led into aperture 37 during swallowing and other activity involving forward tongue movement. Lower ramp member 23 extends through the marginal member above front portion 17 to intersect upper ramp member 33 at the lower edge of aperture 37. This extension of ramp 23 assures that the tongue apex is directed through the aperture as the tongue moves forward and is guided by lower ramp 23 and upper ramp 33. The tactile contact between the tongue tip and the palatal soft tissue has a stenotaxic locating effect.

Lower ramp member 23 extends below marginal member 13 and comprises front portion 41, left side portion 44 and right side portion 47 as indicated in the rear elevational view of FIG. 4. Side portion 44 extends downward from the lower side of inner edge 26 of the marginal member left section 15. Front portion 41 extends downward from the lower side of inner edge 31 of marginal member front section 17 and side portion 47 extends downward from the lower side of inner edge 29 of marginal member right section 20. Front portion 41 and side portions 44 and 47 are angled toward the midline of the lingual aspect of the anterior segment of the lower jaw. Portions 41, 44 and 47 form a generally concave guide for the inferior anterior aspect of the tongue. The rear lower edge formed by lower ramp portions 41, 44 and 47 is generally arc shaped for relief of the restricted lower lingual frenum and to provide a possible resting position for a patient with a finger sucking habit. As is readily seen in the side sectional view of FIG. 3, the ramp shape of member 23 and the extension of the lower ramp through marginal member 13 to aperture 37 allows the tongue to be guided to a proper initial swallowing position. According to the invention, the structure of ramp 23 does not require conscious selection of the upper side of a horizontal shelf-like support structure. Further, it is impossible to avoid the tongue guiding channels in swallowing so that there is no need for the artificial repelling action of sharp protrusions or electrical elements to maintain the tongue in its proper position to initiate rapid swallowing.

Figure 5:
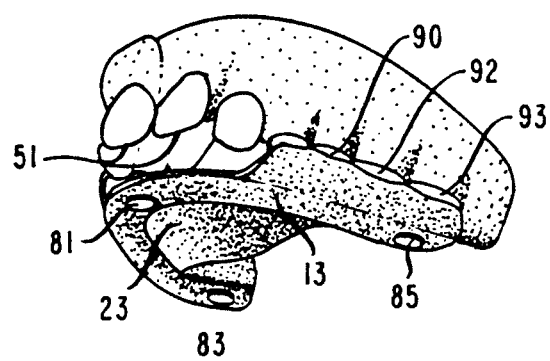
FIG. 5 is a perspective view of the device inserted into the upper jaw of a patient's mouth.

Upper ramp member 33 above marginal member 13 extends upward from the upper side of inner edge 26, the upper side of inner edge 29 and the upper side of inner edge 31 as shown in the top view of FIG. 2 and the rear elevational view of FIG. 4. Member 33 has aperture 37 located so that the tongue apex is directed therethrough to the proper position for initiating a normal swallow. The arch above aperture 37 is relatively narrow so as not to restrict the normal elevation and distal thrust of the dorsal aspect of the tongue during swallowing.

Device 10 as shown in FIG. 5 is usually held in place by the posterior crown undercuts deciduous molars or bicuspids. The device is prefabricated for swallowing problem patients having a dental arches of various sizes. Ramp members 23 and 33 are relatively narrow in width so as to fit a patient with a narrow dental arch. Side members 15 and 20 are relatively wide so that the device may be removably attached to patients having dental arches within a prescribed range. A section 81 on the lower surface of front section 17 of marginal member 13 contacts lower anterior dentition. The inferior or lower surfaces of sides 15 and 20 of marginal member 13 have similar sections 83 and 85 in contact with posterior dentition of the mandibular arch. Sections 81, 83 and 85 are adjusted to provide three simultaneous points of contact for stable positioning of the device in the closed mouth of the wearer. The lower ramp 23 fits freely within the lower jaw while the three contact sections on the bottom of marginal member 13 provide the aforementioned stable contact with the dentition of the lower jaw.

Several arrangements may be used to provide removable retention for dental arches over such a range. In one arrangement, a light activated resin such as TRIAD gel made by Densply of York, Pa. is placed on the upper surfaces of sides 15 and 20 of marginal member 13. The device as depicted in FIGS. 2-5 with the light activated resin thereon is placed in the patient's mouth and pressed against the upper posterior dental arch. The resin is thereby shaped for retention by the anatomy of the dentition of the upper arch and partially set. When the device is removed, the resin is fully cured. After curing, the added resin bonds to the upper surfaces of sections 15 and 20 and is shaped to be retained by the upper buccal dentition. Upon reinsertion for use, device 10 with the added shaped resin is removably retained on the posterior teeth of the upper jaw. A quick setting acrylic may also be used for the same purpose. Tab 32 on front section 17 of the marginal member permits manipulation of device 10 during the formation of the removable retentive layer.

Prior art tongue thrust training appliances have been fabricated by making a cast from an impression of a patient's mouth and a wax bite for orientation. The device is then formed by means of a molding process. As is well known, such a process generally requires the services of a professional well versed in the field of orthodontics as well as highly skilled dental laboratory personnel. It is time consuming and costly and major adjustments in the mouth are often necessary to obtain a suitable fit. In accordance with the invention, the device of FIG. 1 is not formed for a particular patient but is prefabricated to fit a wide range of mouths. The spacing between the inner edge 26 of left section 15 and the inner edge 29 of right section 20 is dimensioned to fit into the narrowest mouth of a prescribed range while the widths of sections 15 and 20 are dimensioned to accommodate the location of upper dentition expected in the prescribed range. There is no need for highly skilled personnel to produce a properly fitting appliance. Thus, the appliance and process of fitting the appliance is more economical.

Figure 6:
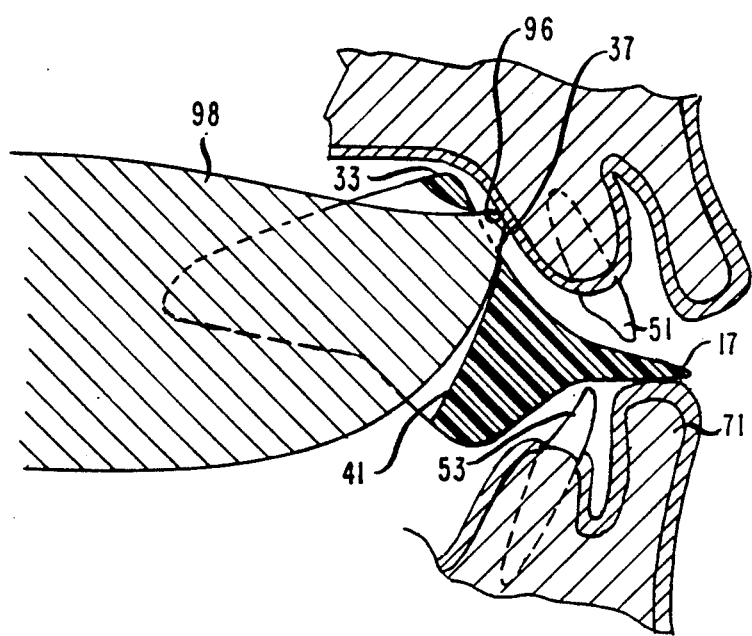
FIG. 6 is a vertical sectional view of a patient's mouth with the device inserted therein taken along the medial center line of the device.

FIG. 6 shows a vertical sectional view of a patient's mouth with the device inserted therein that is taken along the medial center line of the device. In FIG. 6, device 10 previously fitted for a particular patient as aforementioned is shown removably engaged with the teeth in the maxillary arch and supported by contact with teeth in the mandibular arch. The undercuts of the buccal aspect of side teeth 90, 92 and 93 on the left side of the maxillary arch (not shown) retain side 15 of marginal member 13 as shown in FIG. 5. Retention of device 10 is accomplished by means of a closely adapted material such as light activated resin or acrylic above the upper surface of side 15.

Front portion 17 of the marginal member extends between upper anterior teeth 51 and lower anterior teeth 53 while swallowing. Portion 17 slopes downward to allow relief from upper anterior teeth so that they may erupt as they drift backward and downward. Lower ramp 23 redirects the apex 96 of the tongue 98 lingually and upwardly towards the bend of the anterior palate. The apex 96 of tongue 98 is thereby prevented from contacting anterior teeth 51 and 53. According to the invention, the angle of the lower ramp is set so that the device does not cause discomfort or interferes with desired normal jaw closure or tongue movements.

The superior anterior surface of the tongue is guided by upper arch 33 so that the tongue apex 96 the tongue is directed through aperture 37. The tongue apex is thereby put into contact with the anterior bend of the palate for normal swallowing. When the contained tongue and its apex is guided to its initial normal swallowing position, the normal physiological events can proceed without any interference from the device. Advantageously, the device prevents unwanted force between the tongue tip 96 and any anterior teeth 51 or 53 or between upper anterior teeth 51 and surrounding bone and the lower lip 71.

The narrow arch of upper ramp member 33 which is spaced from the palate to avoid tissue irritation allows the upper dorsal aspect of the tongue to elevate itself to rest against the open palate area during normal swallowing. Lower ramp 23 is substantially parallel to the lingual aspect of the mandibular arch so that it does not interfere with normal jaw movement. Ramp 23 in close proximity but spaced from the tissue of the mandibular arch to avoid tissue irritation. The prefabricated construction of the device conforms to the physiological needs of the patient and is comfortable to wear. Most patients who receive treatment utilizing the device are between the ages of seven and twelve. The treatment, however, is effective for children as young as three and may be used throughout adulthood.

The invention has been shown and described with reference to an illustrative embodiment thereof. It is to be understood that various modifications and changes may be made by those skilled in the art without departing from the scope or spirit of the invention.

What is claimed is:

1. A device for oral retraining comprising:
 a body including:
 a marginal segment curved to contact the dentition of the maxillary arch comprising an anterior section and first and second side sections, each side section having a substantially flat upper surface facing posterior dentition of the maxillary arch,
 a first tongue guiding segment joined with and extending below the marginal segment including a channel forming member for directing the inferior surface of the tongue tip upward, the channel forming member having a posteriorly facing entrance for receiving the inferior surface of the anterior portion of the tongue, and
 a second tongue guiding segment joined with and extending above the marginal segment including a channel forming member in proximity to the palate for directing the superior surface of the tongue tip, the channel forming member having a posteriorly facing entrance for receiving the superior surface of the anterior portion of the tongue, the second tongue guiding segment including an anteriorly facing aperture in the channel forming member for guiding the tongue apex into contact with the curved aspect of the anterior palate and soft tissue, and the substantially flat upper surfaces of the first and second side sections of the marginal segment being dimensioned to span a prescribed range of dental arches.

2. A device for oral retraining according to claim 1 wherein the channel forming member of the first tongue guiding segment comprises a ramp portion extending backward and downward from the anterior section of the marginal segment at a prescribed angle to the marginal segment to guide the inferior surface of the tongue tip forward and upward toward the anteriorly facing aperture in the second tongue guiding segment.

3. A device for oral retraining according to claim 2 wherein backward and downward angle of the ramp of first tongue guiding segment channel member is prescribed to allow substantially free jaw movement.

4. A device for oral retraining according to claim 3 wherein the channel forming member of the second tongue guiding segment comprises a ramp portion angled backward and upward from the anterior section of the marginal segment to guide the superior surface of the tongue tip forward and downward toward the anteriorly facing aperture therein.

5. A device for oral retraining according to claim 4 wherein the ramp portion of the second tongue guiding segment channel member is spaced from the palate to avoid contact with palatal tissue.

6. A device for oral retraining according to claim 4 wherein the first tongue guiding segment channel member is spaced from the lingual aspect of the mandibular arch to avoid contact with the tissue thereof.

7. A device for oral retraining according to claim 4 wherein the ramp portion of the first tongue guiding segment extends through the marginal segment at the prescribed angle thereto to the lower edge of the aperture in the second tongue guiding segment.

8. A device for oral retraining according to claim 1 further comprising means on the upper surfaces of the side sections of the marginal member for removably engaging the posterior dentition of the maxillary arch.

9. A device for oral retraining according to claim 8 wherein the removably engaging means comprises at least a layer of material shaped to engage the posterior dentition of the maxillary arch.

10. A device for oral retraining according to claim 9 wherein the layer of material shaped to engage the posterior dentition of the maxillary arch is a light activated resin shaped by insertion against the posterior dentition of the maxillary arch.

11. A device for oral retraining according to claim 9 wherein the layer of material shaped to engage the posterior dentition of the maxillary arch is a partially cured acrylic shaped by insertion against the posterior dentition of the maxillary arch.

12. A device for oral retraining according to claim 1 wherein the marginal member further comprises means on its lower surface for contacting the dentition of the mandibular arch to stabilize the device.

13. A device for oral retraining according to claim 12 wherein the means on the lower surface of the marginal member contacting the dentition of the mandibular arch comprises a plurality of spaced sections adapted to contact the lower dentition to stabilize the device.

14. A device for oral retraining according to claim 13 wherein the plurality of spaced sections adapted to contact the lower dentition comprises at least one section on the lower surface of the anterior section of the marginal member adapted to contact anterior dentition of the mandibular arch and at least one section on the lower surface of each of the side sections of the marginal member adapted to contact posterior dentition of the mandibular arch.

15. A device for oral retraining according to claim 1 wherein the anterior section of the marginal segment is sloped to project forward and downward to the incisal edges of the anterior teeth of the maxillary arch extending over the anterior teeth of the mandibular arch to prevent contact between the lower lip and the maxillary arch dentition.

16. A device for tongue position training adapted to fit a prescribed range of dental arches comprising a body made of acrylic including:

a marginal segment curved to contact the teeth of the upper dental arch comprising an anterior section and a pair of side sections each side section having a flat upper surface facing the upper dental arch of a width spanning the location of side teeth of the prescribed range of dental arches;

a first tongue tip guiding segment joined to a lower surface of the marginal segment including a channel forming member extending below the marginal segment backward and downward from the anterior portion of the marginal segment in proximity to the lingual aspect of the mandibular dentition for controlling the position of the inferior surface of the anterior portion of the tongue, the first tongue tip guiding segment having a posteriorly facing entrance for receiving the inferior surface of the anterior portion of the tongue; and a second tongue tip guiding segment joined to the upper surface of the first portion including a channel forming member extending upward and backward from the anterior portion of the marginal segment in proximity to the palate for controlling the position of the superior surface of the anterior portion of the tongue, the second tongue guiding segment having a posteriorly facing entrance for receiving the superior surface of the anterior portion of the tongue and an anteriorly facing aperture for guiding the tongue apex into contact with the curved aspect of the anterior palate and soft tissue.

17. A device for tongue position training adapted to fit different mouths according to claim 16 wherein the channel of the first tongue guiding segment extends through the marginal segment to the portion of the aperture adjacent to the marginal segment.

18. A device for tongue position training adapted to fit different mouths according to claim 16 wherein the channel of the second tongue guiding segment includes an arch shaped element dimensioned to allow contact of the superior surface of the anterior portion of the tongue with the palate.

19. A device for tongue position training adapted to fit different mouths according to claim 16 wherein the width of the tongue tip guiding segments between the side sections of the marginal segment are dimensioned to fit within the dental arch of the narrowest of the prescribed range of dental arches.

* * * * *